United States Patent [19]

Maullem et al.

[11] Patent Number: 4,839,385

[45] Date of Patent: Jun. 13, 1989

[54] USE OF MANOALIDE AND ITS DERIVATIVES FOR MODIFYING CALCIUM HOMEOSTASIS

[75] Inventors: Shmuel Maullem; George Sachs, both of Los Angeles; Larry Wheeler, Irvine, all of Calif.

[73] Assignees: The Regents of the University of California, Berkeley; Allergan, Inc., Irvine, both of Calif.

[21] Appl. No.: 89,936

[22] Filed: Aug. 25, 1987

Related U.S. Application Data

[63] Continuation of Ser. No. 825,310, Feb. 3, 1986, abandoned.

[51] Int. Cl.$^4$ .............................................. A61K 31/34
[52] U.S. Cl. .................................. 514/473; 514/867; 514/863; 514/927
[58] Field of Search ........................................ 514/473

[56] References Cited

U.S. PATENT DOCUMENTS 4,447,445  5/1984  Jacobs et al. ...................... 514/473

*Primary Examiner*—Frederick E. Waddell
*Attorney, Agent, or Firm*—Irell & Manella

[57] ABSTRACT

Compounds derived form the marine sponge *Laffariella variabilis* and known by the name manoalide, and its derivatives, modify calcium homeostasis.

10 Claims, 1 Drawing Sheet

USE OF MANOALIDE AND ITS DERIVATIVES FOR MODIFYING CALCIUM HOMEOSTASIS

ACKNOWLEDGEMENT OF GOVERNMENT SUPPORT

This invention was made with Government support under grant no. AM-32532 and with the National Institutes of Health and the University of California. The Government has certain rights in this invention.

"This application is a continuation of application Ser. No. 825,310, filed Feb. 3, 1986, now abandoned".

BACKGROUND OF INVENTION

This invention relates to the discovery that manoalide, along with its derivatives, are calcium (Ca) homeostasis modifying drugs. More particularly, this invention relates to such compound's ability to block calcium entry or calcium release from cell stores, calcium dependent processes and calcium pumps.

Elevation of free intracellular cytosolic calcium is a central event (secord messenger) in how cells couple a stimulus (hormone, external signal) to the corresponding response (proliferation, secretion of acid, amylase histamine etc). Cells have two basic mechanisms for raising free intracellular calcium: (i) by opening plasma membrane calcium channels letting calcium extracellular into the cell; and (ii) by release of calcium from intracellular stores.

The effect of manoalide on intracellular calcium levels was investigated through experiments using gastric glands. These glands contain two types of cells that use either plasma membrane channels or release from intracellular stores to increase cytosolic calcium. It has been discovered that at low concentrations, 1 μM and less, manoalide inhibits calcium from entering through the plasma membrane calcium channels. At higher concentrations (30–50 μM) manoalide blocks calcium release from intracellular stores.

Modification of calcium homeostasis by manoalide and related compounds is expected to have application in diseases of the nervous system involving modification of membrane lipids or transmitter release, (Parkinson's, Alzheimer's), diseases of the cardiovascular system involving application of cardiac or vascular smoothe muscle contractility and platelet aggragation (hypertension, cardiac infarction and atherosclerorsis), diseases of the G.I. tract such as ulcer disease, diarrhea, motility due to secretion of acid or $Cl^-$, diseases of the kidney involving renal handling and of fluid and electrolytes (metabolic acidosis, alkalosis), disease of abnormal growth (neoplasia, psoriasis).

SCOPE OF THE INVENTION

The compounds of this invention, manoalide and a number of its derivatives, have been isolated from the marine sponge *Luffariella variabilis* or derived from those isolates.

Manoalide and seco-manoalide have been published by E. D. de Silva and P. J. Scheuer; Tetrahedron Letters Vol 21, pp 1611–1614, Perganon Press Ltd. 1980. They have the following structures.

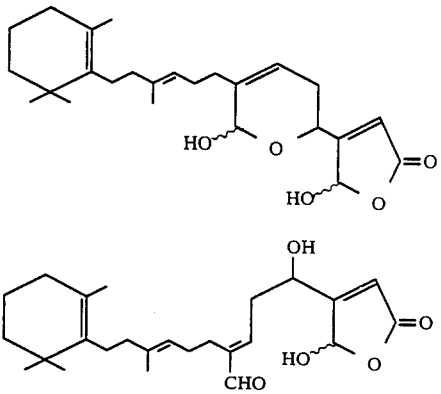

These compounds, and dehydro-seco-manoalide, an artifact of isolation, have also been disclosed in U.S. Pat. No. 4,447,445 where they are described as having anti-inflammatory, analgesic and immunosuppressive activity.

Several derivatives and analogs of manoalide have been isolated from *L. variabilis* or prepared by synthetic means. Generically they can be represented by the formula:

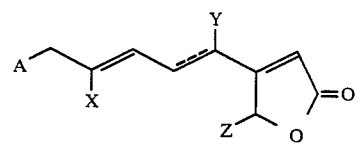

wherein
X is $-CH_3$, $-CH_2OH$, $-CHO$, OR $-COOH$;
Y is $-H$ or $-OH$;
Z is $-H$ or $-OH$; and
the dotted line represents either a single bond or a double bond which may be in either the E or Z configuration; and
A is $R_m$ or $R_n$

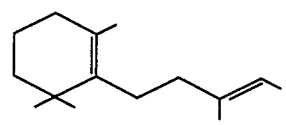

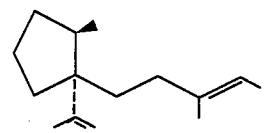

When Y is $-OH$ and Z is $-CHO$ or $-COOH$, the compound of formula II includes the hemiacetal or delta-lactone, respectively.

When X is $-COOH$, the compounds of formula I may be in the form of the corresponding alkyl esters, esters derived from alcohols of 1 to 10 carbon atoms. When X is $-CH_2OH$ and/or Y is $-OH$ and/or Z is —OH, the compounds of formula I may be in the form of the acyl esters of acids from 1 to 10 carbon atoms.

Also included are the pharmaceutically acceptable salts derived from these compounds where X or Z is —COOH.

SUMMARY OF THE INVENTION

This invention covers a method for modifying calcium homeostasis in a mammal and thereby treating diseases affected by the modification of calcium homeostasis, which method comprises administering to a mammal a therapeutically effective amount of a compound of formula I alone or in combination with a pharmaceutically acceptable excipient.

PREFERRED EMBODIMENTS

Compounds of the invention which contain alcohols may conveniently be esterified with acyl groups containing 1–10 carbon atoms using methods standard in the art. Suitable acyl groups include acetyl, propanoyl, n-hexanoyl, 4-methylpentanoyl, and the like. The acyl groups may also be unsaturated, and thus also included are acryloyl, methyl acryloyl, 3-methylbuten-2-oyl, and so forth.

In addition, for those embodiments wherein X is carboxyl and are not in a lactone form, the esters of the free carboxyl groups are also included in the invention. These are esters of the saturated or unsaturated alcohols, such as, for example, ethanol, n-butanol, cyclohexanol, cyclopentanol, 3-methylbuten-2-ol, i-propanol, and the like.

The esters of the compounds of formula I containing alcohol constituents may be prepared using standard techniques, such as treating the alcohol-containing compounds of the invention with the free acid forms of the desired acyl substituent in the presence of a strong acid such as boron trifluoride, hydrogen chloride, or sulfuric acid. (They may also be formed from the activated forms of the acyl groups, such as the acyl chlorides.) The reaction can be carried out in an inert organic solvent in which the free acids and the alcohols are soluble, such as a hydrocarbon solvent, for example, cyclooctane, cyclohexane, or benzene, or a halogenated hydrocarbon solvent such as chloroform or dichloroethane, or an ether solvent such as diethyl ether or tetrahydrofururan. The reaction is conducted at from about 0° C. to the reflux temperature of the reaction mixture, preferably using hydrogen chloride as a catalyst at a temperature for the reaction mixture of 15° C.-35° C.

The esters of carboxyl groups contained in formula 1, i.e., when X is COOH, are prepared in a similar manner, except using the appropriate alcohol as reagent.

The product is isolated by conventional means, such as dilution of the reaction mixture with water and extraction at a suitable pH with a water immiscible organic solvent.

Certain of the compounds of the invention contain chiral centers, and accordingly may be prepared as enantiomeric or diastereomeric mixtures or in optically pure form. Unless otherwise specified herein, the preparations are racemates at each chiral center. However, the scope of the invention is not to be considered as limited to these forms, but also to encompass the individual optical isomers of the compounds. Where the chiral center corresponds to a chiral center in the natural product analogs, the naturally occurring chirality is preferred.

Similarly, the double bonds may be present in the Z or E forms or mixtures thereof. However, the stereochemistry corresponding to that of the analogous natural product is preferred.

PREFERRED EMBODIMENTS

The following compounds are illustrative of particularly preferred embodiments of the invention. The table below lists the substituents and, where available, the trivial names associated with these substituents. In several cases, both the open chain and cyclic forms (lactones aor hemiacetals) are included. The symbols $R_m$ and $R_n$ refer to the terpenoid substituents set forth above.

| A | X | Y | Z | | Trivial Name |
|---|---|---|---|---|---|
| $R_m$ | $CH_2OH$ | OH | H | single | manoalide diol |
| $R_m$ | COOH (free acid) | OH | OH | single | — |
| $R_m$ | COOH (lactone) | OH | OH | single | manoalide δ-lactone |
| $R_m$ | CHO | H | OH | double(E) | dehydro-seco-manoalide |
| $R_m$ | CHO (hemiacetal) | OH | H | single | — |
| $R_m$ | $CH_3$ | H | OH | double(E) | — |
| $R_m$ | $CH_3$ | H | OH | single | luffariel-lolide |
| $R_m$ | $CH_3$ | OH | H | single | — |
| $R_m$ | CHO (hemiacetal) | OH | OH | single | manoalide |
| $R_m$ | CHO | OH | OH | single | seco-manoalide |
| $R_n$ | $CH_2OH$ | OH | H | single | — |
| $R_n$ | COOH (free acid) | OH | OH | single | — |
| $R_n$ | COOH (lactone) | OH | OH | single | — |
| $R_n$ | CHO | H | OH | double(E) | — |
| $R_n$ | CHO (hemiacetal) | OH | H | single | — |
| $R_n$ | $CH_3$ | H | OH | double(E) | — |
| $R_n$ | $CH_3$ | H | OH | single | — |
| $R_n$ | $CH_3$ | OH | H | single | — |
| $R_n$ | CHO (hemiacetal) | OH | OH | single | luffariel-lin A |
| $R_n$ | CHO | OH | OH | single | luffariel-lin B |

Utility and Administration

The compounds of the invention are shown hereinbelow to modify calcium homeostasis. Accordingly, these compounds are useful in the control of a number of conditions as outlined above. For such uses, the compounds of the invention are administered to mammals, including humans, in an effective amount of about 0.1 to 50 mg per day per kilogram of body weight. The drugs may be administered topically, orally, parenterally, or by other standard administration routes.

Parenteral administration is generally by injection, either subcutaneously, intramuscularly, or intravenously. Injectables can be prepared in conventional suspension or solution forms, as emulsions, or as solid forms suitable for reconstitution. Suitable excipients are, for example, water, saline, dextrose, Hank's solution, Ringer's solution, glycerol, and the like. In addition, the compositions may contain small amounts of nontoxic auxiliary substances, such as wetting or emulsifying agents, pH buffering agents, and so forth. Standard methods for formulating pharmaceuticals of this type may be found in *Remington's Pharmaceutical Sciences*, Mack Publishing Company, Easton PA (latest edition).

For oral administration, suitable excipients include mannitol, lactose, starch, magnesium stearate, talcum, glucose, magnesium carbonate, and so forth. Oral compositions take the form of solutions, suspensions, tablets, pills, capsules, powders, sustained release formulations, and the like.

The following examples are intended to illustrate the invention and are not limiting. Parts and percentages are given by weight unless otherwise indicated.

EXAMPLE 1

Preparation of 3,7-Bis(hydroxymethyl)-4-hydroxy-11-methyl-13-(2,6,6-trimethylcyclohexenyl)-2,6,10-tridecatrienoic acid γ-lactone (manoalide diol)

A. Excess sodium borohydride (300 mg, 7.0 mM) was added in small portions to a stirred solution of manoalide (136 mg, 0.33 mM) in isopropanol (20 mL) at 0° C. for one hour. Excess reagent was destroyed by dropwise addition of 2% hydrochloric acid until hydrogen evolution ceased. The product was partitioned between water (100 mL) and ether (2×100 mL), the ether extract dried over sodium sulfate and then solvent removed to obtain an oil. The product was purified by HPLC to obtain the diol. Yield 75 mg (55% theoretical); oil*; $^1$H NMR (CDCl$_3$)δ 0.99 (s, 6H), 1.60 (s, 3H), 1.65 (s, 3H), 4.11 (d, 1H, J=14Hz), 4.17 (d, 1H, J=14 Hz), 5.39 (t, 1H, J=7Hz), 5.98 (br s, 1H); HRMS. m/z 402.2770, C$_{25}$H$_{38}$O$_4$ requires 402.2770.
*IR(film) 3350, 1775 cm$^{-1}$

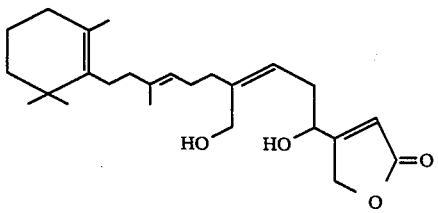

B. Manoalide diol, as prepared in paragraph A, is dissolved in acetic anhydride in threefold molar excess in the presence of base, and the mixture stirred at room temperature for several hours. The solvents are then removed and the residue dissolved in ether and filtered to obtain a clear filtrate. Crystals of the diacetate are obtained from the filtrate. In a similar manner, but substituting for acetic anhydride the halides of the appropiatre carboxylic acids, the proprionate, dipropionate, hexanoate, and dipentanoate are prepared.

EXAMPLE 2

Preparation of manoalide δ-lactone

A solution of Jone's reagent (prepared from chromium trioxide [6 mL] was added dropwise to a stirred solution of manoalide (30 mg, 0.07 mM) in distilled acetone (20 mL) at 25° C. until the solution remained brown. After five minutes, the reaction mixture was filtered through a short column of silica gel and the solvent evaporated to obtain an oil. The product was chromatographed by HPLC to obtain the manoalide δ-lactone as a mixture of two diastereoisomers. Yield 15 mg (50% theoretical); oil*; $^1$H NMR (CDCl$_3$)δ 0.99 (s, 6H), 1.60 (s, 3H), 1.65 (s, 3H), 5.10 (m, 1H), 5.26 (dd, 0.5H, J=12, 5 Hz), 5.37 (dd, 0.5H, J=12, 5 Hz), 6.15 (s, 0.5H), 6.20 (d, 0.5H, J=7 Hz), 6.23 (s, 0.5H); HRMS. m/z 414.2384, C$_{25}$H$_{34}$O$_5$ requires 414.2406.

*IR (film) 3300, 1770, 1740 cm$^{-1}$; UV(MeOH) 208.5 nm (ε 10,350)

Monoalide δ-lactone is an inseparable 1:1 mixture of diastereoisomers resulting from epimerization at the hemiacetal carbon atom.

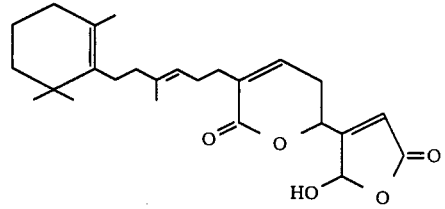

EXAMPLE 3

Preparation manoalide δ-lactone acetate

A. Manoalide δ-lactone (15 mg. 0.04 mM) was dissolved in acetic anhydride (0.5 mL) and pyridine (1.0 mL) and the mixture was stirred at 25° C. for four hours. The solvents were removed under high vacumm and the residue dissolved in ether and filtered through a silica gel plug to obtain a clear oil. The oil was chromatographed by HPLC to obtain a mixture of diastereoisomeric acetates. Yield 16 mg (quantitative); oil;* $^1$H NMR (CDCl$_3$)δ 0.99 (s, 3H), 1.59 (s, 3H), 1.65 (s, 3H), 2.18 (s, 3H), 5.10 (t, 1H, J=7 Hz), 5.21 (m, 1H), 6.26 (s, 0.4H), 6.34 (s, 0.6H), 6.61 (m, 1H), 6.98 (s, 1H) HRMS. m/z 456.2514, C$_{27}$H$_{36}$O$_6$ requires 456.2512.
*IR(film) 1880, 1770, 1725 cm$^{-1}$; UV(MeOH) 208 nm (ε 10,600)

Manoalide δ-lactone acetate is a 6:4 mixture of two diastereoisomers. The diastereoisomers can be separated, but the material assayed was the mixture of isomers.

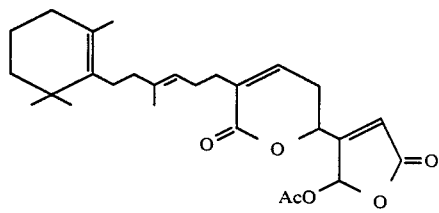

B. In a manner similar to that set forth in Paragraph A, but substituting for acetic anhydride, the anyhydrides or halides of proprionic, butanoic, pentanoic, or hexanoic acid, the corresponding manoalide δ-lactone proprionate, butanoate, pentanoate, and hexanoate are prepared.

EXAMPLE 4

Isolation and Characterization of Dehydro-seco-manoalide

Examination of UV and $^1$H NMR data of the crude extracts of the sponge Luffariella variabilis provide evidence that dehydro-seco-manoalide is formed during chromatographic purification of these extracts, presumably by acid-catalyzed dehydration of manoalide on silica.

The isolation and purification of manoalide may utilize two or three chromatographic separations on silica gel. Fractions that eluted before manoalide were saved and certain fractions, distinguished by their $^1$H NMR spectra, combined. The combined fractions were chromatographed by LC on μ-Porasil using diethyl ether as eluant to obtain dehydro-manoalide as a viscous yellow oil. The yield is variable.

UV (EtOH) 316 nm ($\epsilon$ 12,000), 205 nm ($\epsilon$ 10,300).

UV (EtOH+NaOH) 461 nm ($\epsilon$ 25,000), 280 nm ($\epsilon$ 1600). 246 ($\epsilon$ 2000).

IR (CHCl$_3$) 1745 cm$^{-1}$, 1670 cm$^{-1}$.

$^1$H NMR (CDCl$_3$)$\delta$ 0.96 (s, 6H), 1.56 (s, 3H), 1.60 (s, 3H), 5.11 (br t, 1H, J=7 Hz), 6.14 (s, 1H), 6.32 (s, 1H), 6.82 (d, 1H, J=15.5 Hz), 6.91 (d, 1H, J =5 Hz), 7.34 (dd, 1H, J=15.5, 6 Hz), 9.52 (s, 1H). $^{13}$C NMR (CDCl$_3$)$\delta$ 194.3 (d), 171.5 (s), 160.0 (d), 146.3 (s), 145.8 (d), 137.8 (s), 136.8 (s), 133.8 (s), 128.3 (d), 126.9 (s), 121.8 (d), 119.5 (d), 97.8 (d), 40.1 (t), 39.7 (t), 34.8 (s), 32.6 (t), 29.5 (t), 28.5 (q), 28.5 (q), 27.7 (t) 24.6 (t), 19.7 (q), 19.4 (t), 16.0 (q).

Mass spectrum, m/z (%), 398 (3), 380 (3), 251 (6), 137 (100).

Mass measurement, m/z=398.2429, C$_{25}$H$_{34}$O$_4$ requires 398.2457.

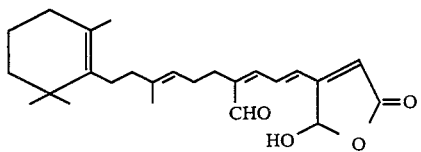

Using methods analogous to those of Example 3, Paragraph B, and standard in the art, the acetate, formate, hexanoate, and pentanoate esters of dehydro-seco-manoalide are prepared.

EXAMPLE 5

Isolation and Characterization of 3-(4,8-dimethyl-10-(2,6,6-trimethylcyclohexenyl)-deca, 7-dienyl)-4-hydroxybutenolide (Luffariellolide)

A previously unidentified sponge was collected by hand using SCUBA (−15 to −20 m) at Palau, Western Carolines Islands in January, 1985 and stored frozen. The specimen was defrosted and blended in a high-speed blender with hexane (700 mL) for 2 minutes. the resulting suspension was vigorously stirred for 30 minutes and then filtered. Fresh hexane (700 mL) was added and the mixture was again stirred for 30 minutes and filtered. The combined hexane extracts were evaporated to obtain a brown oil (14.43 g). A portion of the oil was purified by chromatography on silica (MPLC) using hexanes:EtOAc (4:1) to obtain luffariellolide as a colorless oil.

UV:(CH$_3$OH) 214 nm ($\epsilon$ 10,000), (CH$_3$OH/OH$^-$) 253 nm ($\epsilon$ 4400);

$^H$NMR (CDCl$_3$)$\delta$ 6.01 (br s, 1H), 5.85 (br s, 1H), 5.14 (br t, 2H, J=7 Hz), 1.64 (br s, 6H), 1.60 (br s, 3H), 0.99 (s, 6H); $^{13}$C NMR (CDCl$_3$)$\delta$ 171.9 (s), 169.9 (s), 136.9 (s), 136.8 (s), 136.0 (s), 126.6 (s), 123.1 (d), 121.9 (d), 117.0 (s), 99.5 (d), 40.1 (t), 39.7 (t), 39.5 (t), 34.8 (s), 32.6 (t), 28.5 (q), 27.8 (t), 27.7 (t), 26.4 (t), 24.9 (t), 19.7 (q), 19.4 (t), 16.0 (q), 15.9 (q);

High resolution mass spectrum, obsd. m/z 386.2821, C$_{25}$H$_{38}$O$_3$ requires 386.2821.

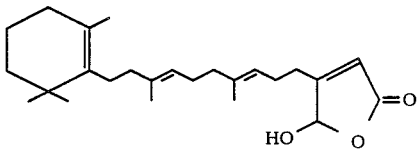

EXAMPLE 6

Isolation and Characterization of Luffariellin A and Luffariellin B

About 5% of the specimens of Luffariella variabilis collected at Palau during the period Jan. 9, 1985 and Jan. 23, 1985 contained two new compounds, luffariellin A and luffariellin B in place of the normal metabolites manoalide and seco-manoalide. These specimens were identified by extracting a small portion of each specimen and analyzing the $^1$H NMR spectrum of the crude extracts.

The frozen sponge was soaked in methanol overnight, and the methanol was then decanted and filtered. This procedure was repeated 3 times. The combined extracts were evaporated, and the resulting slurry was partitioned between water and dichloromethane (5×250 mL). The combined extracts were dried over anhydrous sodium sulfate and evaporated to obtain a brown oil (670 mg). The oil was filtered through a short column of silica gel in 1:1 hexane/ethyl acetate, then chromatographed on a Lobar B silica column using 25% ethyl acetate in hexane, then 1:1 ethyl acetate/hexane was eluants to obtin luffariellin A (126 mg) and luffariellin B (63 mg).

*Luffariellin A*: oil.

IR (CHCl$_3$) 3310 (br), 1780, 1762 cm$^{-1}$.

UV (MeOH) 230 nm (4800).

$^1$H NMR (CDCl$_3$)$\delta$ 0.70 (d, 3H, J=7 Hz), 1.59 (s, 3H), 1.68 (s, 3H), 4.64 (s, 1H), 4.82 (s, 1H), 4.85 (m, 1H), 5.09 (br t, 1H, J=7 Hz), 5.34 (s, 1H), 5.70 (s, 1H), 6.08 (s, 1H); $^{13}$C NMR (CDCl$_3$)$\delta$ 172.0/171.8 (s), 169.0/168.3 (s), 148.0 (s), 137.2/137.0 (s), 136.7 (s), 122.6 (d), 120.9/120.6 (d), 117.8/116.7 (d), 111.6 (t), 98.3/97.8 (d), 91.3/91.1 (d), 63.1/62.3 (d), 55.1 (s), 41.8 (d), 39.6/39.4 (t), 34.8 (t), 34.3 (t), 32.4 (t), 31.0 (t) 29.4 (t), 25.9 (t), 20.7 (t), 20.7 (q), 18.1 (q), 16.2 (q).

Mass spectrum, m/z 398 (M-H$_2$O).

*Luffariellin B*: oil.

IR (CHCl$_3$) 3350 (br), 1762, 1686 cm$^{-1}$.

UV (MeOH) 226 nm (10,000).

$^1$H NMR (CDCl$_3$)$\delta$ 0.70 (d, 3H, J=7 Hz), 1.55 (s, 3H) 1.67 (s, 3H), 4.63 (s, 1H), 4.82 (s, 1H), 5.07 (br t, 1H, J=7 Hz), 5.40 (m, 1H), 6.111 (br s, 2H), 6.56 (t, 1H, J=7 Hz), 9.40 (s, 1H); $^{13}$C NMR (CDCl$_3$)$\delta$ 195.2 (d), 171.2 (s), 170.4/169.3 (s), 148.3/148.2 (s), 145.7/145.6 (d), 137.4 (s), 122.2 (d), 118.3 (d), 117.7 (t), 98.3/97.9 (d), 66.8/66.3 (d), 55.1 (s), 41.9 (d), 34.8 (2C, t), 31.0 (t), 29.1 (t), 26.8 (t), 24.5 (t), 20.7 (t), 20.7 (q), 18.1 (a), 16.3 (q).

MS m/z 398 (M-G$_2$O).

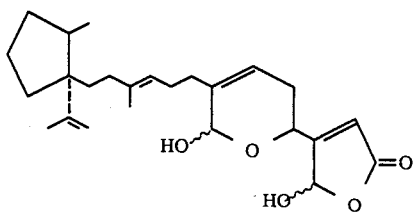

Luffariellin A

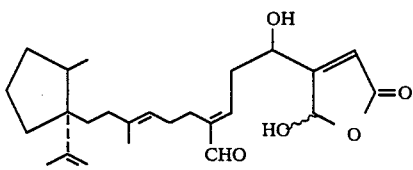

Luffariellin B

EXAMPLE 7

Effect of Manoalide on Calcium Levels in Mouse spleen cells

Conconavalin A (Con A) has been shown to raise intracellular calcium. When 40 μg/ml Con A was added to single cell suspensions of mouse spleen cells were prepared by the standard methods, a rapid rise in intracellular calcium was observed. This calcium signal is characteristic of calcium moving from outside the cell to inside through a plasma membrane channel. If calcium is removed from the external medium, the rise in intracellular calcium is completely absent.

The concentration of free intracellular calcium was determined by loading the cells with a calcium sensitive florescent dye, FURA-2 ® (Grynkiewicz, G., Poenig, M. and Tsien, R. J., Biol. Chem 260: 3440–3450, 1985). Fluorescence measurements and calibration curves were done the same as for Quin-2, Pandol, S., Schoeffield, M., Sachs, G. and Muallem, S. (J. Biol. Chem 10081–10086, 1985).

Once the cells were loaded, aliquots ($10^6$ cells/ml) were placed in cuvettes and the baseline intracellular calcium concentration determined.

Manoalide was dissolved in polyethylene glycol 400 or dimethylsulfoxide and added as indicated before the Con A was added to the cuvette.

Preincubation of mouse cells for 5 minutes at 37° C. with 0.5 μM manoalide resulted in the complete inhibition of the rise in intracellular calcium normally elicited with addition of 40 μg/ml of Con A. The inhibition of the calcium signal was time dependent and irreversible.

Similar results were obtained with human lymphocytes isolated and prepared according to the method of Muallem, et al.

Table 1 shows a dose response curve for both types of cells.

TABLE 1

| Cell type | Conc. MLD (μM) | % Inhibition Calcium rise* |
|---|---|---|
| Mouse spleen cells | .01 | 0 |
| | .1 | 30 |
| | .3 | 70 |
| | 1.0 | 100 |
| Human lymphocytes | .05 | 0 |
| | .1 | 15 |
| | 0.25 | 30 |

TABLE 1-continued

| Cell type | Conc. MLD (μM) | % Inhibition Calcium rise* |
|---|---|---|
| | 0.5 | 65 |
| | 1.0 | 100 |

*All cells were preincubated at 37° C. for 5 minutes before addition of Con A (40 μg/ml).

EXAMPLE 8

Modification of Ca in Gastric Gland Cells

Gastric glands contain both peptic cells (release of calcium from intracellular stores) and parietal cells (plasma membrane calcium channel). Gastric cells were isolated as described by Muallem, et. al. (Amer. J. Physiol. 248-G216-G228, 1985). Addition of CCK or carbachol to a final concentration of 2.5 mM and 0.1 mM respectively were used to activate these cells. Muallem et al. (J. Biol. Chem.: In Press, 1986) have shown that these hormones stimulate these cells and result in an increase in free intracellular cytosolic calcium.

(a) Parietal Cells

Parietal cells have been shown to rise cytosolic calcium by opening plasma membrane calcium channels after stimulation with CCK or carbachol. The result of activation is acid secretion. If these cells are loaded with Fura-2 and stimulated with the above hormones, a calcium signal similar to the one in FIG. 1 is observed.

Preincubation with 0.1–5.0 μM of manoalide blocked acid secretion in parietal cells indicating manoalide at these concentrations blocks the elevation of cytosolic calcium. Table 2 shows the results of these incubations.

TABLE 2

| | Acid Secretion | |
|---|---|---|
| MLD Conc (μM) | Carbachol Stimulation | Forskolin |
| 0 | 100% | 100% |
| 0.1 | 50 | 100 |
| 0.5 | 10 | 100 |
| 5.0 | 0 | 100 |
| 50 | 0 | 100 |

(b) Peptic Cells

With peptic cells, the hormones CCK or carbachol cause release of calcium from intracellular stores. Incubation of these cells with 5 μM manoalide shows no inhibition of CCK of carbachol stimulated increase in calcium. The calcium signal in these cells is different from that observed in the conconavalin stimulated release of calcium from spleen cells.

The calcium transient observed is characteristic of the release of calcium from intracellular stores. If calcium is removed from the extracellular medium it has no effect on the calcium signal.

To examine the correlation between secretion and the calcium signal, the effects of manoalide on pepsin secretion were quantitated (Table 3).

TABLE 3

| MLD Conc | CCK Stimulation (N = 5) | Carbachol (2) | Forskolin (2) |
|---|---|---|---|
| 0 μM | 100% of control | 100% | 100% |
| 0.1 | 100 | 100 | 100 |
| 0.5 | 105 | 110 | 100 |
| 5.0 | 115 | 110 | 100 |

TABLE 3-continued

| MLD Conc | CCK Stimulation (N = 5) | Carbachol (2) | Forskolin (2) |
|---|---|---|---|
| 50 | 60 | 40 | 100 |

No inhibition of the biological effect was observed until cells were incubated with >50 μM manoalide.

Concentrations of 50 μM manoalide, or higher, showed inhibition of the calcium signal for example, administration of 60 μM manolide showed significant inhibition of the calcium signal.

This effect was irreversible and time dependent.

EXAMPLE 9

Effect on Human Carcimona Cells (A431)

The A431 cell line, human epidermoid carcinoma cell, can be activated with 5 μg/ml epidermal growth factor (EGF). Sawyer, S. T. and Cohen, S (Biochemistry 20, 6280-6286, 1981) have shown that EGF enhances calcium uptake in these cells.

A431 Cells were grown in 150 ml Falcon flasks containing Dulbecco's modified Eagle's medium (Gibco) supplemented with 10% fetal calf serum (Irvine Scientific) and gentamycin.

The free intracellular cytosolic concentration of calcium in A431 and the effect of EGF (5 μg/ml) are shown in FIG. 1A. Incubation of A431 cells for 5 minutes with 1.5 μM manoalide resulted in complete abolition of the CA signal (FIG. 1B).

These effects are shown in FIG. 2.

Other tumor cell lines which can be inhibited from growing by manoalide are EL-4.

What is claimed is:

1. A method for controlling a condition treatable by modifying calcium homeostasis in a mammal, wherein said condition is hypertension, cardiac infarction, atherosclerosis, ulcer, diarrhea, motility due to secretion of acid or Cl−, metabolic acidosis, alkalosis, or psoriasis, which method comprises:
   administering an amount of a compound of formula I effective to treat hypertension, cardiac infarction, atherosclerosis, ulcer, diarrhea, motility due to secretion of acid or Cl−, metabolic acidosis, alkalosis, or psoriasis, alone or in combination with a pharmaceutically acceptable excipient, to a mammal in need thereof, where formula I is

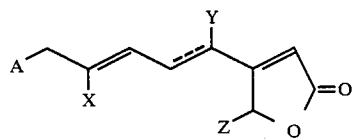

wherein
X is —CH$_3$, —CH$_2$OH, —CHO, or —COOH;
Y is —H or —OH;
Z is H or OH; and
the dotted line represents either a single bond or a double bond which may be in either the E or Z configuration; and
A is Rm or Rn

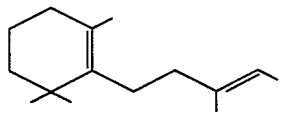

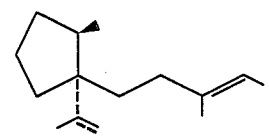

and where Y is —OH and X is —CHO or —COOH, the compound of formula I includes the hemiacetal or deltalactone, respectively; and
when X is —COOH, the corresponding alkyl esters derived from alcohols of 1 to 10 carbon atoms; and
when X is —CH$_2$OH and/or Y is —OH and/or Z is —OH, the corresponding acyl esters of acids from 1 to 10 carbon atoms; and
the pharmaceutically acceptable salts derived from those compounds where X is —COOH.

2. The method of claim 1 where the compound is manoalide.

3. The method of claim 1 where the compound is seco-manoalide.

4. The method of claim 1 wherein the disease is hypertension.

5. The method of claim 1 for treating cardiac infarction.

6. The method of claim 1 for treating athersclerorsis.

7. The method of claim 1 for treating ulcers.

8. The method of claim 1 for treating diarrhea.

9. The method of claim 1, wherein the compound of formula I is administered in combination with a pharmaceutically acceptable excipient at a concentration of 1M or less.

10. The method of claim 1, wherein the compound of formula I is administered in combination with a pharmaceutically acceptable excipient at a concentration of between about 30 to about 50 μM.

* * * * *

UNITED STATES PATENT AND TRADEMARK OFFICE
CERTIFICATE OF CORRECTION

PATENT NO. : 4,839,385

DATED : June 13, 1989

INVENTOR(S) : Shmuel Muallen, et al.

It is certified that error appears in the above-identified patent and that said Letters Patent is hereby corrected as shown below:

On the title page, under item [19] and in item [75], delete "Maullen" and insert --Muallen--.

Col. 1, lines 12 & 13, delete quotation marks preceding "This" and following "abandoned".

Col. 1, line 49, change "smoothe" to --smooth--.

Col. 6, line 2, change "Monoalide" to --Manoalide--.

Signed and Sealed this

Sixteenth Day of April, 1991

Attest:

HARRY F. MANBECK, JR.

Attesting Officer

Commissioner of Patents and Trademarks